United States Patent [19]

Joachim

[11] Patent Number: 4,768,517
[45] Date of Patent: Sep. 6, 1988

[54] METHOD AND APPARATUS FOR SECURING HAIR TO SKIN SECTIONS BY LASER APPLICATION

[76] Inventor: Czech Joachim, Jahnstr. 19, 8405 Donaustauf, Fed. Rep. of Germany

[21] Appl. No.: 120,668

[22] Filed: Nov. 16, 1987

[51] Int. Cl.⁴ .............................................. A61B 17/00
[52] U.S. Cl. ...................................... 128/330; 623/15
[58] Field of Search ............. 128/303.1, 330, 395–398; 623/15

[56] References Cited

U.S. PATENT DOCUMENTS

| | | | |
|---|---|---|---|
| 3,062,214 | 11/1962 | Maxwell | 623/15 |
| 3,862,453 | 1/1975 | Widdifield | 128/330 |
| 4,103,365 | 8/1978 | Applegate | 128/330 |

*Primary Examiner*—Max Hindenburg
*Attorney, Agent, or Firm*—James E. Nilles; Donald C. McGaughey

[57] ABSTRACT

The invention relates to a method and apparatus for securing hairs to skin sections, particularly for improving or reconstituting a hair garnishing of the scalp, wherein at least an attachment end of donor's hair is contacted with said skin section or the base of residual hair and is subsequently fused therewith by means of a laser beam.

The apparatus for performing the method comprises an applicator head including a laser beam source and donor's hair guide means permitting the centered advance and positioning of the attachment end of the donor's hair on the attachment point defined by the point of impingement of an emitted laser beam on a skin section or on an existing residual hair adjacent the skin section whereat the donor's hair is to be attached. The attachment process itself is prepared with the aid of optical means for positional correlation between the laser beam and the donor's hair.

26 Claims, 1 Drawing Sheet

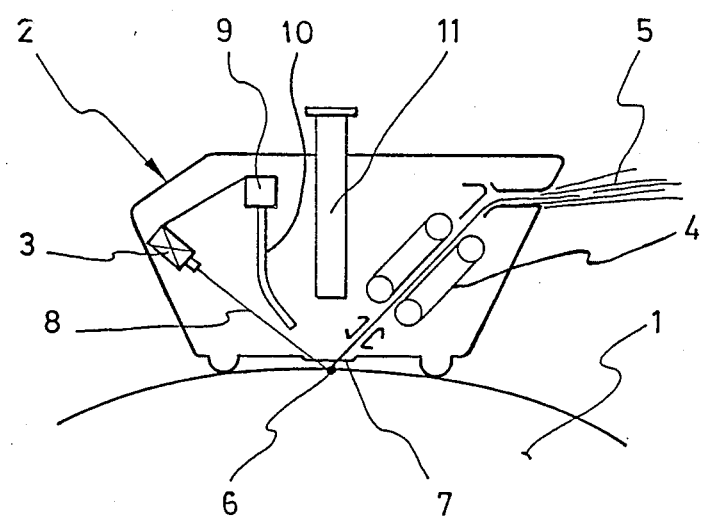

METHOD AND APPARATUS FOR SECURING HAIR TO SKIN SECTIONS BY LASER APPLICATION

BACKGROUND OF THE INVENTION

The present invention relates to a method for securing hairs to a skin section which may or may not have residual hairs thereon, particularly for the purpose of improving or reconstituting the hair-garnishing of a scalp. The invention is also directed to apparatus for performing this method.

Numerous chemical compositions are known as remedies for alopecia or baldness, which mainly afflicts human males, and for the promotion of renewed hair growth after the onset of baldness, although the effectiveness of such compositions have remained rather unsatisfactory. This applies in particular to all efforts to promote renewed hair growth at locations of the scalp which are already afflicted by a complete loss of hair.

The employ of toupees, hairpieces and wigs involves many technical and aesthetical problems frequently resulting in considerable discomfort to the user.

Hair transplantations have also been performed by taking sections of the scalp, with the hair growing thereon, from areas not yet or only slightly affected by hair loss, and transplanting such sections into areas of the scalp so afflicted by baldness. It has been found, however, that the hair originally growing on such transplanted scalp sections tends to fall out, with the result that hair loss is also incurred by reason of the transplantation from the unafflicted areas. Further, such transplantations result in the formation of additional conspicuous scars on the areas afflicted by hair loss.

It is therefore an object of the invention to provide a method of the type defined in the introduction, by means of which it is possible to permanently replace the lost hair garnishing to thereby retain a completely natural appearance, particularly at the location of the hairline.

It is a further object of the invention to provide an apparatus permitting the method defined above in an uncomplicated manner with extremely accurate localization of the point of application and with minimum discomfort to the person subjected to such method.

It is a still further object of the invention to provide a method that can be performed preferentially in service facilities of the cosmetic trade.

SUMMARY OF THE INVENTION

The method consists either in contacting the attachment end of donor's hair with an attachment point on a desired scalp area and subsequently fusing the donor's hair with the respective skin section by means of a laser beam, or, if there is residual hair growth, in contacting the attchment end of the donor's hair with the selected skin section immediately adjacent the base point of the residual hair, and in subsequently fusing the donor's hair with the residual hair adjacent the respective skin section. The method may also consist in fusing donor's hair to both the skin section and the residual hair.

The donor's hair is preferably separated into single hairs, the attchment end of each hair being placed in contact with the desired skin section, preferably a scalp section, at an attachment point onto which the laser beam is then directed.

The laser beam permits a very high energy density to be rapidly obtained on a punctate area, which constitutes the attachment point for the donor's hair, resulting in a momentary increase of flexibility of the upper skin layers in connection with a softening of the attachment end of a hair or hair tuft, with the result that the donor's hair's body is intimately fused with the attachment point on the selected skin section. For accurately positioning and orientating the attachment end of the donor's hair and for achieving adequate control, it is advantageous if the attachment point, i.e. the point of impingement of the laser beam on the skin, or on a residual hair as will be explained hereinafter, is optically demarcated prior to the donor's hair being fused therewith.

If the skin still carries residual hair, although of an insufficiently developed nature, the base point of such residual hair may preferably be used as an attachment point for securing a new hair separated from donor's hair, with the result, that the local heat stress of the scalp is drastically reduced. In this case, the new hair is fused with the residual hair by means of the laser beam as closely as possible to the scalp or to both the residual hair and the scalp.

Therefore, in accord with the above summary, the phrase "attachment point" is defined to mean either the skin at a specific point on a selected skin section, which may be on the scalp or elsewhere, or a specific portion of a residual hair, or both as is the case when the attachment end of donor's hair is fused to both the scalp and the residual hair. The skin and the specific hair portion are basically equivalents for the purpose of the invention.

The apparatus for performing this method comprises a movable applicator head enclosing a laser beam source, an applicator opening in the head, and a guide means for placing the attachment end of donor's hair at a selected attachment point. The attachment end of the donor's hair is advanced by the guide means through the applicator opening of the applicator head into contact with the attachment point on the selected skin section, whereupon the laser beam emitted by the laser beam source then impinges on the skin section at the attachment point.

The attachment point may be defined by the base point of a residual hair still present on the respective scalp section, in which case the donor's hair is directly fused with the residual hair adjacent the scalp section.

The apparatus is preferably provided also with optical demarcation means for permitting the attachment end of the hair or hair tuft to be accurately positioned with respect to the attachment point, and at the same time for permitting the performance of the method to be optically controlled.

BRIEF DESCRIPTION OF THE DRAWINGS

The drawing is a diagrammatical section view of an applicator head embodying the invention.

DETAILED DESCRIPTION OF THE PREFERRED EMBODIMENT OF THE INVENTION

An embodiment of the invention shall now be described by way of example with reference to the accompanying drawing.

For the permanent attachment of donor's hair to a scalp 1 afflicted by alopecia, the invention employs an applicator head 2, having a housing, preferably made of plastic, which includes a flexible bottom wall. The main functional components of the applicator head comprise a laser beam source 3 and a guide means arrangement 4, the latter serving for feeding and positioning donor's hair 5, which may be supplied in the form of hair tufts. Usually, however, individual hairs 5 are separated from a donor's hair supply prior to application, each hair 5 so separated being advanced through an applicator opening 7 at the bottom wall of the applicator head, so that its attachment end projects a slight distance therefrom, the attachment point 6, i.e. the point of contact of the attachment end of each hair 5 with scalp 1 coinciding with the point of impingement of the laser beam 8 emitted by laser beam source 3 on the scalp.

In the context of the present invention, "donor's hair" may denote natural hair of other persons, but also of the person whose hair garnishing is to be improved according to the invention. It is thus absolutely within the scope of the present invention to employ a person's own hair as "donor's hair", which may, for instance, be cut at areas of the scalp still enjoying healthy hair growth.

The attachment point 6 may also be demarcated independently of laser beam 8 by means of optical demarcation means 9 preferably employing an optical conductor cable 10 in combination with a light source for this purpose. It is, of course, also possible for this purpose to employ a projector tube operable to project a demarcating light point onto the scalp 1 for demarcating the attachment point. Prefrably, the demarcating light point corresponds in size to the area of the scalp 1 on which laser beam 8 impinges.

The laser beam source 3 is preferably a $CO_2$ laser to thereby avoid undesirable effects in the lower skin layers.

Also provided, preferably in combination with an enlargement means, is an observation tube 11 permitting visual observation of the area defined by the attchment point 6, at which the attachment end of the donor's hair tuft 5 contacts the scalp and upon which the laser beam 8 emitted by laser beam source 3 impinges. In this manner it is possible to visually monitor the preparation of the hair application process as well as the actual fusing of hair 5 by means of laser beam 8. The obsevation tube 11 is therefore preferably in the form of a microscope.

The guide means 4 is also operable to fix hair 5 in position for fusing and for releasing the hair from the thus fixed position after it has been fused to scalp 1. The guide means 4 includes a feed means for feeding donor's hairs, a centering means for separating out individual hairs and/or centering donor's hairs in a desired position, and a holder means for holding individual or tufts of hairs captive in a selected position. The feed means, in turn, may comprise a feed roller means. The apparatus is further provided with manually operable correction means (not shown) for the hair feed means arrangement, permitting the latter to be accurately positioned at all times with respect to a selected attachment point.

A manually operable correction means is particularly required when the bottom wall of the housing of applicator head 2, through which applicator opening 7 extends, is of a flexible or resilient construction, or when the bottom face of applicator head 2 is provided with resilient contact bodies for improving the adaptability of applicator head 2 to the contour of the selected area of scalp 1. For facilitating displacement of applicator head 2 on scalp 1, the bottom face of applicator head 2 may be provided with rollers or casters which may simultaneously be used for determining the distance of applicator opening 7 from scalp 1. If so required, the background brightness of the area observed through tube 11 may be improved by the provision, within applicator head 2, of a light source of reduced luminosity, this light source being not shown, however, in the diagrammatic illustration of the applicator head 2.

The applicator head for performing the above explained method operates as follows.

After the applicator head has been placed on the selected area of scalp 1, the attachment point is demarcated with the aid of demarcation means 9, whereupon guide means 4 is operated to advance donor's hair of a desired length and color and place its attachment end with scalp 1. With the aid of observation tube 11, the position of the thus advanced hair 5 may then be corrected, so that the attachment end of a hair or hair tuft contacts scalp 1 accurately at the attachment point 6 indicated by demarcation means 9. Subsequently, laser beam source 3 is activated for generating a high-energy laser beam 8 to thereby create an instantaneous high energy density, i.e. a high heat density at the attachment point 6, that is, at the contact area between scalp 1 and hair 5. This results in a localized increase of flexibility of the scalp in combination with a melt-softening of hair 5, as a result of which the attachment end of hair 5 is fused with scalp 1, so that the donor's hair 5 is intimately and permanently connected to the scalp after termination of the instantaneous laser beam application.

The same operation is subsequently repeated at each adjacent attachment point upon the supply of each further hair 5, so that donor's hairs may be connected to scalp 1 in a very dense array.

The functionality of applicator head 2 may be modified within a wide range, for instance, by widening guide means 4 in such a manner that it is capable of dividing a tuft of donor's hair supplied thereto into individual hairs or smaller hair tufts and of arranging a closely spaced row of the attachment ends of such hairs o hair tufts to project from the bottom side of applicator head 2. Guide means of this type preferably is used in combination with a movable laser beam source 3. After optical verification of at least one attachment point 6, the laser beam source 3 may then be moved relative to guide means 4 to thereby direct or aim the laser beam at the attachment point and when energized, fuse the hairs or hair tufts 5, supplied via guide means 4, with the scalp 1. The guide means may also comprise funnel-shaped components consolidating, condensing or compacting the attachment ends of donor's hair tufts, or means for separating out individual hairs.

The fusing process may be promoted by the additional supply of an additive, preferably polyvinyl pyrrolidone, to the attachment point 6.

While the guide means may be mounted to be movable to place hair 5 in position for fusing as above described, it is, of course, also possible to mount guide means 4 at a fixed position, so that the attachment point 6 is determined by the attachment end of the advanced hair 5 projecting through applicator opening 7. In this case the laser beam source is mounted for movement relative to the head housing and demarcation means 9 is fixedly coupled to the laser beam source 3 for movement in unison therewith. The demarcation means 9, and thus also laser beam source 3, is adapted to be visually aligned with the attachment point 6 determined in this case by the attachment end of the hair 5, whereupon laser beam 8 is used in the manner already described for fusing the attachment end of hair 5 to the scalp at the attachment point 6. The thus accomplished alignment of laser beam source 3 and/or guide means 4 permits any variation of the distance between applicator head 2 or its applicator opening 7, respectively, and scalp 1, possibly caused by the curvature of the head, to be compensated for, so that the intersection of laser beam 8 and the feed plane of hair 5 will always be accurately positioned in the scalp plane containing the attachment point 6. It may also be desirable to place the attachment end of the donor's hair 5 in contact with attachment point 6 while maintaining the donor's hair in a substantially perpendicular alignment relative to scalp 1. In this case, guide means 4 may comprise a substantially vertical guide funnel which would be positioned at the location of the observation tube in the arrangement shown in the drawing.

The novel method as well as the associated apparatus in the form of applicator head 2 are adapted to be performed and applied in an extremely simple manner, so that applicator head 2 may be readily employed in the cosmetic services trade. The high energy density at the attachment point permits the donor's hair to be substantially instantaneously fused with the scalp to thereby avoid any substantial discomfort to the patient. The invention provides ample choice with respect to the pattern and density of the donor's hair to be attached.

It may be advantageous to employ rather "strong" hair for the fusing process, i.e. hair having a relatively large diameter as encountered, for instance, on members of Far-Eastern or South American populations.

In a modified version of the method, it is also possible to prepare the fusing process by creating a micro-recess in scalp 1 at the attachment poin 6, in which the attachment end of hair 5 is subsequently received. After insertion of hair 5, this recess is then melt-filled by use of laser beam 8, preferably with the addition of an embedding or fusing additive. In this manner, it is possible to improve the intimacy of the fused connection between the donor's hair 5 and the scalp.

In this case, the apparatus for performing the method additionally includes a needle element with associated actuating means (not shown) for forming the micro-recess in preparation of the actual fusing process. Also provided in this case is a container for containing a liquid additive for promoting the embedding and fusing process, in combination with suitable feed means within the apparatus for supplying such additive to the point of application.

The invention has been explained hereinabove with reference to an embodiment in which donor's hair is fused directly with the scalp to act as a substitute for natural hair. According to a further aspect of the invention, the donor's hair may also be fused with residual hair on the scalp 1 of the person concerned. Individual residual hairs, the natural growth of which is already likewise impaired, are frequently encountered in areas of the scalp substantially bereft of their hair garnishing. This residual hair, possibly is short or if need be it may be shortened to a desired length, is particularly well suited for employment as the base or attachment point for the fusing of new hair 5 therewith.

In this case, a donor's hair 5 is contacted with scalp 1 immediately at the "base point" of the residual hair, where the latter emerges from scalp 1, so that the new donor's hair 5 contacts both the scalp 1 and the residual hair immediately at the point of contact of the donor's hair with scalp 1. The actual fusing by means of laser beam 8 will then be carried out at a point slightly above scalp 1 by a punctate laser beam fusing of the new donor's hair 5 immediately with the residual hair. The fusing point should be situated as closely to scalp 1 as possible. The new donor's hair may, if need be, also be fused partially with the residual hair and with the scalp 1.

The possibility of utilizing residual hair offers the considerable advantages of fushing materials of identical structure and of avoiding even microscopical changes in the scalp, to thereby further reduce the discomfort to the person undergoing the hair substitution treatment, at least in those areas occupied by residual hair.

The invention thus makes it possible to at least drastically reduce the disconcerting consequences of the hitherto not fundamentally eradicable alopecia, and to provide a hair garnishing which for the first time can approximate the appearance of the original hair growth.

I claim:

1. A method for securing an attachment end of donor's hair (5) to an attachment point (6) on skin sections (1), possibly having residual hair thereon, particularly for the improvement or reconstitution of the hair-garnishing of the scalp, wherein said method comprises:
   selecting an attachment point (6) on said skin section;
   placing said attachment end of donor's hair (5) in contact with said attachment point; and
   fusing said donor's hair attachment end with said skin section at said attachment point and/or with said residual hair by activating a laser beam (8) to impinge thereat.

2. A method according to claim 1, wherein said donor's hair is in the form of separate individual hairs (5) each having an attachment end which is fused to said attachment point.

3. A method according to claim 2, including the additional steps of
   orientating said laser beam to impinge on a point on said skin section, said impingement point determining said attachment point of said attachment ends of donor's hair (5);
   moving said hair to place said attachment end in contact with said attachment point according to said placing step; and
   holding said hair captive after said attachment end is located at said attachment point for fusing according to said fusing step.

4. A method according to claim 2 including the additional step of
   visually monitoring the positioning of said hair (5) with respect to said attachment point (6) during the placing step.

5. A method according to claim 2 including the additional step of
   determining a plurality of attachment points; and
   displacing and guiding said laser beam (8) along a path of displacement, said path of displacement of said laser beam on said scalp (1) interconnecting said plurality of attachment points (6) whereat said attachment ends (6) of respective hairs (5) or donor's hair tufts are positioned.

6. A method according to claim 2, including the further steps of
   placing each said attachment end of a plurality of donor's hairs (5) in contact with a respective attachment point on said scalp (1) and
   successively fusing said attachment ends to said attachment points on said scalp (1) by changing the direction of said laser beam (8).

7. A method according to claim 1, wherein said skin sections have relatively short residual hairs each having a base point on said skin section (1) which establishes said respective attachment point (6) and wherein said placing step includes placing said attachment end of each donor hair (5) in contact with said skin section adjacent said base point of one of said residual hairs followed by fusing according to said fusing step.

8. A method according to claim 7 including the additional step of
visually monitoring the positioning of said hair (5) with respect to said attachment point (6) during said placing step.

9. A method according to claim 7 including the additional step of
determining a plurality of attachment points;
displacing and guiding said laser beam (8) along a path of displacement, said path of displacement of said laser beam on said scalp (1) interconnecting said plurality of attachment points (6) whereat said attachment ends (6) of respective hairs (5) or donor's hair tufts are positioned.

10. A method according to claim 7, including the further step of
placing each said attachment end of a plurality of donor's hairs (5) individually in contact with an attachment point which is defined by said base point of one of said residual hairs and said skin section adjacent said base point, and
fusing said attachment ends with said residual hairs at each respective defined attachment point (6) by changing the orientation of said laser beam (8).

11. A method according to claim 7 including the further steps of
placing each said attachment end of a plurality of donor's hairs (5) individually in contact with an attachment point constituted by a respective one of said residual hairs; and
fusing each of said attachment ends with its respective residual hair by changing the orientation of said laser beam (8).

12. A method according to claim 1, including the additional steps of:
collecting donor's hair into hair tufts;
compacting said donor's hair tufts at said attachment ends; and
placing said attachment ends in contact with said skin section of said scalp (1) at an attachment point thereon, and
impinging said laser beam (8) on said scalp (1) at said attachment point (6) according to said fusing step.

13. A method according to claim 1, including the additional steps of:
collecting donor's hair in the form of tufts;
separating said tufts into individual hairs prior to being fused; and
subsequently fusing each of said attachment ends separately to its respective attachment point according to said fusing step.

14. A method according to claim 1, including the additional step of
optically demarcating said attachment point prior to said placing and fusing steps.

15. An apparatus for attaching donor's hairs (5) to a skin section (1), said donor's hairs each having an attachment end and said skin section having attachment points (6), said apparatus comprising an applicator head (2) movable relative to said skin section; said applicator head having an applicator opening (7), a guide means (4) mounted in said head for receiving donor's hairs and advancing said attachment end of donor's hair through said applicator opening into contact with said attachment point, and a laser beam source (3) mounted in said head for emitting a laser beam when activated, said laser beam being aimed at said attachment point to impinge on the intersection of said attachment end of donor's hair with said attachment point to fuse the donor's hairs to the skin section.

16. Apparatus according to claim 15, wherein an optical demarcation means (9) including an optical conductor cable (10) is mounted in said applicator head.

17. Apparatus according to claim 15 wherein an optical observation means (11), is mounted in said applicator head.

18. Apparatus according to claim 15 wherein said guide means (4) includes feed means for feeding said donor's hairs, a centering means for centering said donor's hairs and a holder means for holding said donor's hairs in a selected position.

19. Apparatus according to claim 18, wherein said guide means (4) includes a feed roller means.

20. Apparatus according to claim 19, wherein said donor's hair is in tufts and wherein said feed roller means acts to separate individual hairs (5) from said tufts.

21. Apparatus according to claim 18, wherein said donor's hair is in tufts, wherein said guide means receives donor's hair tufts, and wherein said centering means separates out and centers individual hairs (5).

22. Apparatus according to claim 18, wherein said guide means includes means for forming individual donor's hair from a donor's hair tuft.

23. Apparatus according to claim 15, wherein said guide means (4) has means for feeding a plurality of hairs (5) to respective attachment points (6), and means for mounting said laser beam source (3) in said applicator head for movement relative to said guide means (4).

24. Apparatus according to claim 15, wherein said applicator head (2) has a plastic housing which includes a bottom wall, said bottom wall being flexible.

25. Apparatus according to claim 15, wherein said applicator head (2) has a housing which includes a bottom wall, said bottom wall having resilient contact bodies mounted thereon.

26. Apparatus according to claim 24, wherein said bottom wall has support bodies, at least adjacent said applicator opening (7), projecting therefrom to keep said bottom ball at a predetermined distance from said skin section when in use.

* * * * *

UNITED STATES PATENT AND TRADEMARK OFFICE
CERTIFICATE OF CORRECTION

PATENT NO. : 4,768,517
DATED : September 6, 1988
INVENTOR(S) : Joachim Czech

It is certified that error appears in the above-identified patent and that said Letters Patent is hereby corrected as shown below:

On the title page under United States Patent Item (19) "Joachim" should read -- Czech --.

Item (76) Inventor should read -- Joachim Czech --.

Signed and Sealed this

Third Day of January, 1989

Attest:

DONALD J. QUIGG

*Attesting Officer*   *Commissioner of Patents and Trademarks*